(12) United States Patent
Youd et al.

(10) Patent No.: US 10,674,974 B1
(45) Date of Patent: Jun. 9, 2020

(54) CLAMPING MECHANISM FOR A PORTABLE X-RAY IMAGING DEVICE

(71) Applicant: Turner Imaging Systems, Inc., Orem, UT (US)

(72) Inventors: Thomas L. Youd, Salt Lake City, UT (US); Douglas P. Hansen, Spanish Fork, UT (US)

(73) Assignee: TURNER IMAGING SYSTEMS, INC., Orem, UT (US)

( * ) Notice: Subject to any disclaimer, the term of this patent is extended or adjusted under 35 U.S.C. 154(b) by 0 days.

(21) Appl. No.: 16/199,070

(22) Filed: Nov. 23, 2018

(51) Int. Cl.
*A61B 6/00* (2006.01)

(52) U.S. Cl.
CPC .......... *A61B 6/4411* (2013.01); *A61B 6/4405* (2013.01); *A61B 6/4441* (2013.01)

(58) Field of Classification Search
CPC .... A61B 6/4405; A61B 6/4411; A61B 6/4441
See application file for complete search history.

(56) References Cited

U.S. PATENT DOCUMENTS

| 2,355,066 | A |  | 8/1944 | Goldfield et al. |
| 5,499,284 | A |  | 3/1996 | Pellegrino et al. |
| 2008/0020332 | A1 | * | 1/2008 | Lavenda ............ A61B 6/4233 430/495.1 |
| 2012/0076264 | A1 |  | 3/2012 | Ohta et al. |
| 2012/0148031 | A1 |  | 6/2012 | Eaves et al. |
| 2014/0177797 | A1 |  | 6/2014 | Ogura et al. |
| 2018/0108447 | A1 |  | 4/2018 | Turner et al. |
| 2019/0175128 | A1 |  | 6/2019 | Eaves et al. |

FOREIGN PATENT DOCUMENTS

WO 0019781 A2 4/2000

OTHER PUBLICATIONS

The International Search Report and the Written Opinion of the International Searching Authority, PCT Application Serial No. PCT/US19/62650 (dated Feb. 5, 2020) 14 pages.

* cited by examiner

*Primary Examiner* — Mark R Gaworecki
(74) *Attorney, Agent, or Firm* — Kenneth E. Horton; Kirton McConkie

(57) ABSTRACT

Clamping mechanisms that assist with the operation of small, portable x-ray devices are described. A support structure contains a clamping device for a portable X-ray device having a C-arm and a bottom containing a cradle configured to abut and support a C-arm of the portable x-ray device, a mounting plate configured to support a bottom portion of the portable x-ray device. The mounting plate has length members with ridges and a width member extending between the length members, a registration insert configured to mate with an opening in the portable x-ray device, and two clamps configured to secure the portable x-ray device to a cradle and the mounting plate. This clamping device allows the portable x-ray device to be quickly and easily attached to, and detached from, the support structure using only a single hand, while simultaneously preventing the portable x-ray device from accidentally being removed. Other embodiments are described.

21 Claims, 13 Drawing Sheets

CLAMPING MECHANISM FOR A PORTABLE X-RAY IMAGING DEVICE

FIELD

This application relates generally to X-ray equipment. More specifically, this application relates to clamping mechanisms that are used to assist with the operation of small, portable x-ray devices.

BACKGROUND

X-ray imaging systems typically contain an X-ray source and an X-ray detector. X-rays (or other types of radiation) is emitted from the source and impinges on the X-ray detector to provide an X-ray image of the object or objects that are placed between the X-ray source and the detector. The X-ray detector is often an image intensifier or even a flat panel digital detector. In some configurations, these devices contain a C-arm assembly with the source and detector on opposite ends of the "C" arm of the assembly. The C-arm assembly can move through continuous rotation angles relative to the object in order to acquire images from multiple orientations.

Some X-ray imaging systems have limited mobility since they contain a gantry that is secured to a floor, wall, or ceiling. Other imaging systems are more portable since they contain a mobile base (on wheels) and so they can be used in a variety of clinical environments, such as radiology and surgery departments of a medical facility. In either case, the gantry or mobile base is attached to the X-ray imaging device in a permanent or semi-permanent fashion, such that removing the C-arm from the supporting assembly is not done routinely and quickly.

SUMMARY

This application relates generally to clamping mechanisms that are used to assist with the operation of small, portable x-ray devices. In particular, this application describes a support structure with a clamping device for a portable X-ray device having a C-arm and a bottom which contains a cradle configured to abut and support a C-arm of the portable x-ray device, a mounting plate configured to support a bottom portion of the portable x-ray device wherein the mounting plate has length members with ridges and a width member extending between the length members, a registration insert configured to mate with an opening in the portable x-ray device, and two clamps configured to secure the portable x-ray device to the cradle and the mounting plate. Using such a clamping device allows the portable x-ray device to be quickly and easily attached to, and detached from, the support structure by the average person using only a single hand, while simultaneously preventing the portable x-ray device from accidentally being removed.

BRIEF DESCRIPTION OF THE DRAWINGS

The following description can be better understood in light of the Figures which show various embodiments and configurations of the X-ray devices.

Figure 1:
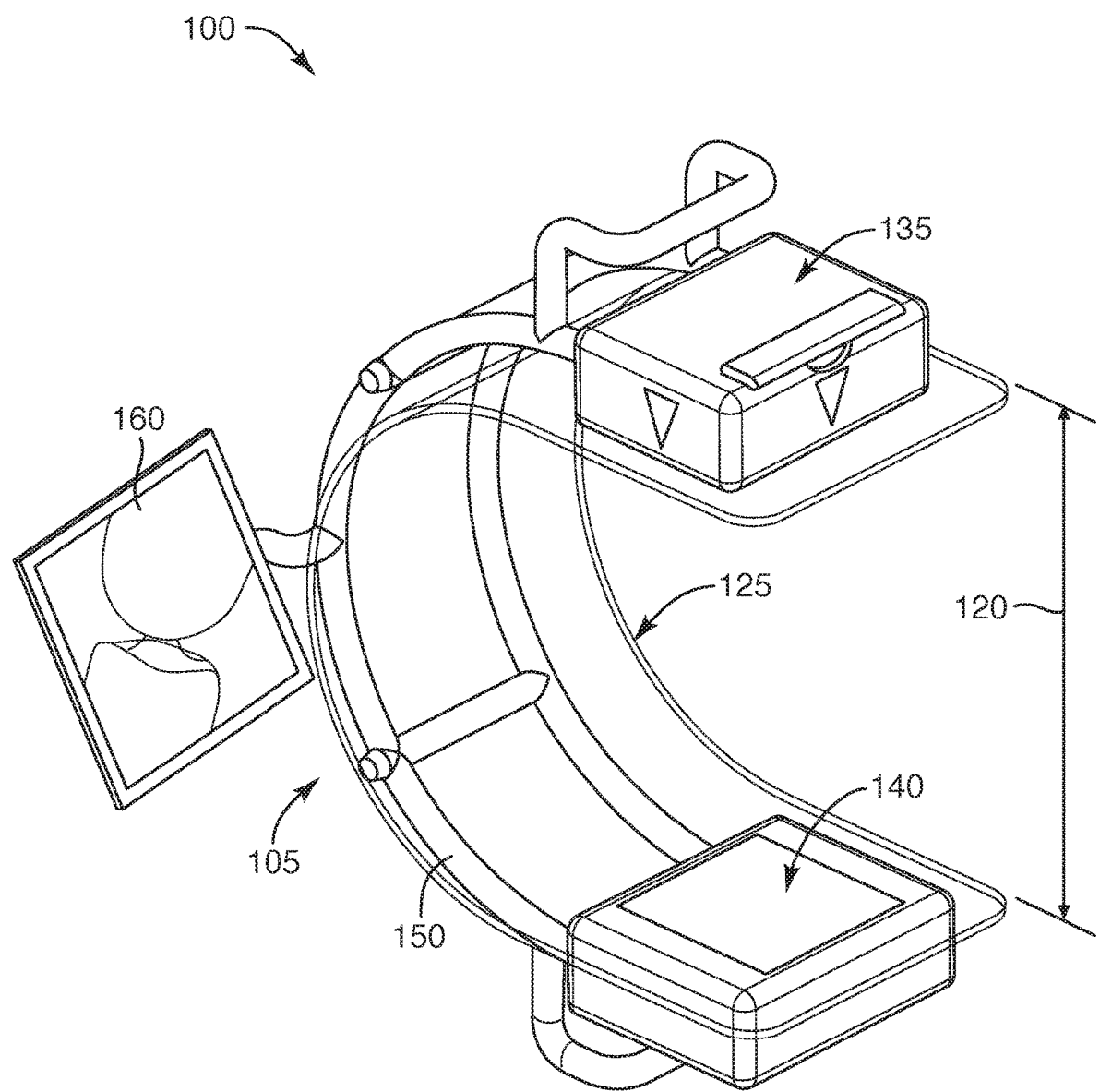
FIG. 1 shows a view of some embodiments of small, portable X-ray devices.

Together with the following description, the Figures demonstrate and explain the principles of the structures, methods, and systems described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray devices can be implemented and used without employing these specific details. Indeed, the described systems and methods related to X-ray devices can be placed into practice by modifying the described systems and methods and can be used in conjunction with any other apparatus and techniques conventionally used in the industry. For example, while the description below focuses on clamping mechanisms for C-arm x-ray devices, the clamping mechanisms can be used with other X-ray imaging arms and x-ray devices, including U-arms or portable x-ray devices that are configured to approximate the C-arm configuration.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

FIG. 1 shows some embodiments of small, portable X-ray devices 100 that can be attached to and held by the supporting devices described herein. Generally, the portable X-ray devices 100 contain an imaging arm that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1.

The C-arm 105 can contain any X-ray source 135 and X-ray detector 140 that allow the X-ray system 100 to take X-ray images. The X-ray source 135 can contain any source that generates and emits X-rays, including a standard stationary anode X-ray source, a microfocus x-ray source, a rotating anode x-ray source, and/or a fluoroscopic X-ray source. And the X-ray detector 140 can contain any detector that detects X-rays, including an image intensifier, a CMOS camera and/or a digital flat panel detector. In some configurations, the detector can have a substantially square shape with a length ranging from about 13 cm to about 15 cm. In other configurations, the detector can have a substantially rectangular shape with the shorter dimension ranging from 12 cm to 16 cm, and the longer dimension ranging from 18 cm to 24 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing can also enclose a removable power source (such as a battery) and optionally a power supply. Thus, the power source and the power supply can be located internal to the housing and also to the x-ray device 100. The supporting electronics for the power source and the power supply, as well as the supporting electronics for an image display and for wireless data upload, can also be located internal to the housing. Thus, in these configurations, the x-ray device 100 does not contain an external power cord or data cable. Incorporating the power source (i.e., the battery), the power supply, and the supporting electronics all within the housing allows the size and the weight of the device to be reduced. With such a configuration, the power source can easily be replaced and delivers 60 or more x-ray images using a single charge. Of course, if needed, the x-ray device can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

The X-ray device 100 also contains a frame 150 that has an open configuration. As shown in FIG. 1, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since other conventional C-arms can't be held in the hands while being operated because they do not have a suitable frame and because they are too heavy.

Figure 2:
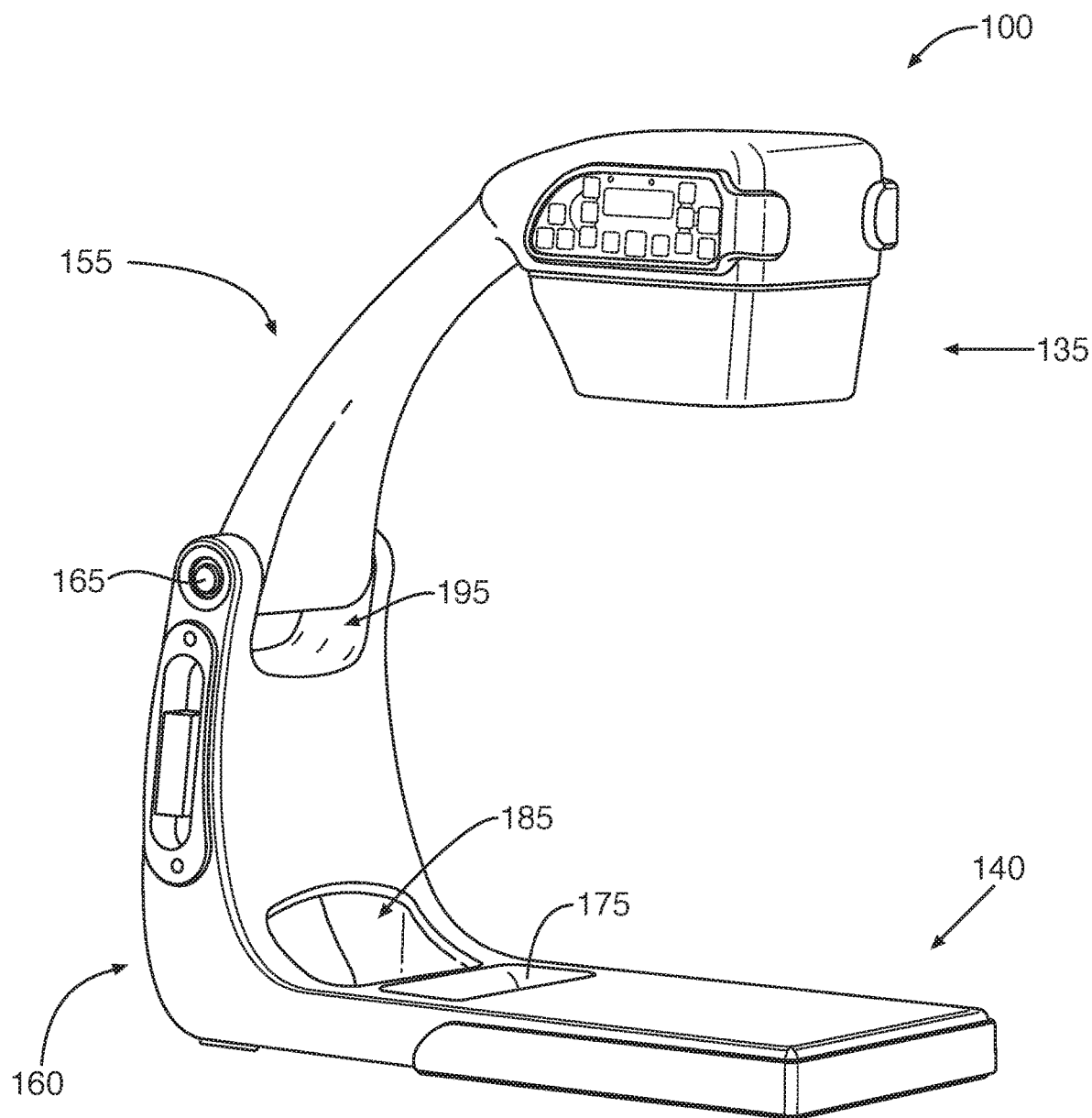
FIG. 2 shows another view of some embodiments of small, portable X-ray devices.

In other embodiments, the portable x-ray device has the configuration as illustrated in FIG. 2. In the embodiments of FIG. 2, the frame 150 has a first portion 155 that is part of the housing that also contains the x-ray source 135 and the associated electronics. The frame 150 also has a second portion 160 that is part of the housing that also contains the x-ray detector 140 and the associated electronics. The first portion 155 of the housing and the second portion 160 of the housing are connected using hinge 165. The bottom of the portable x-ray device can contain an opening 175.

The portable x-ray device 100 has several features not exhibited by other C-arm devices. First, it has the capability of wireless data transfer, thereby eliminating the need for any wired connections or cables to the C-arm. Second, it is internally powered by a battery or internal power source and, therefore, more portable than other C-arm devices which require a power cable. Third, it is lighter that other C-arm devices. As a comparison, the portable x-ray C-arm devices 100 described herein can have a weight ranging from about 10 to about 25 pounds while other C-arm devices have a weight ranging from about 35 to about 375 pounds. In other embodiments, the portable x-ray C-arm devices 100 described herein can have a weight ranging from about 12 to about 18 pounds.

Figure 3A:
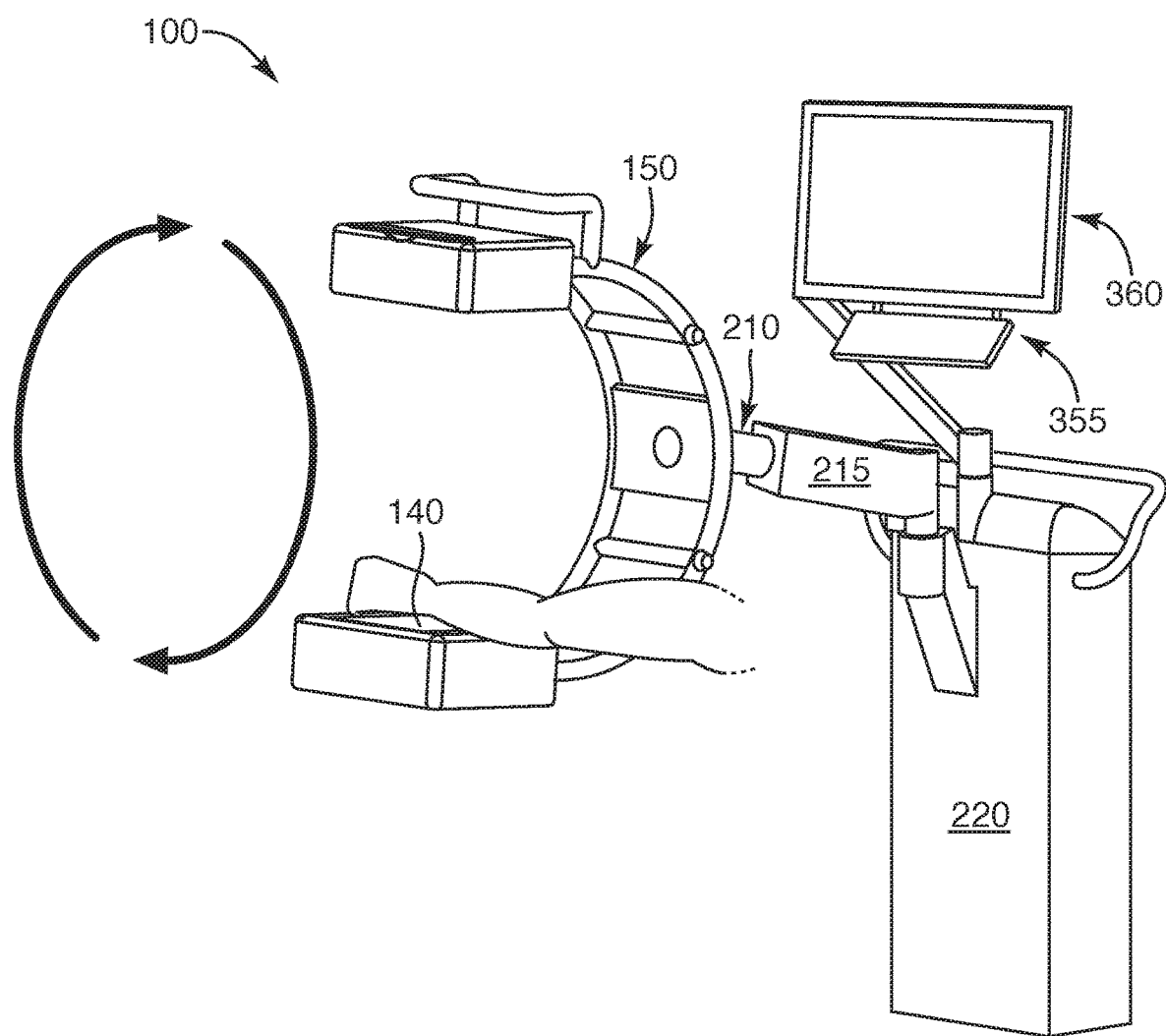
FIGS. 3A and 3B show some embodiments of supporting devices that can be used with small, portable X-ray devices.
Figure 3B:
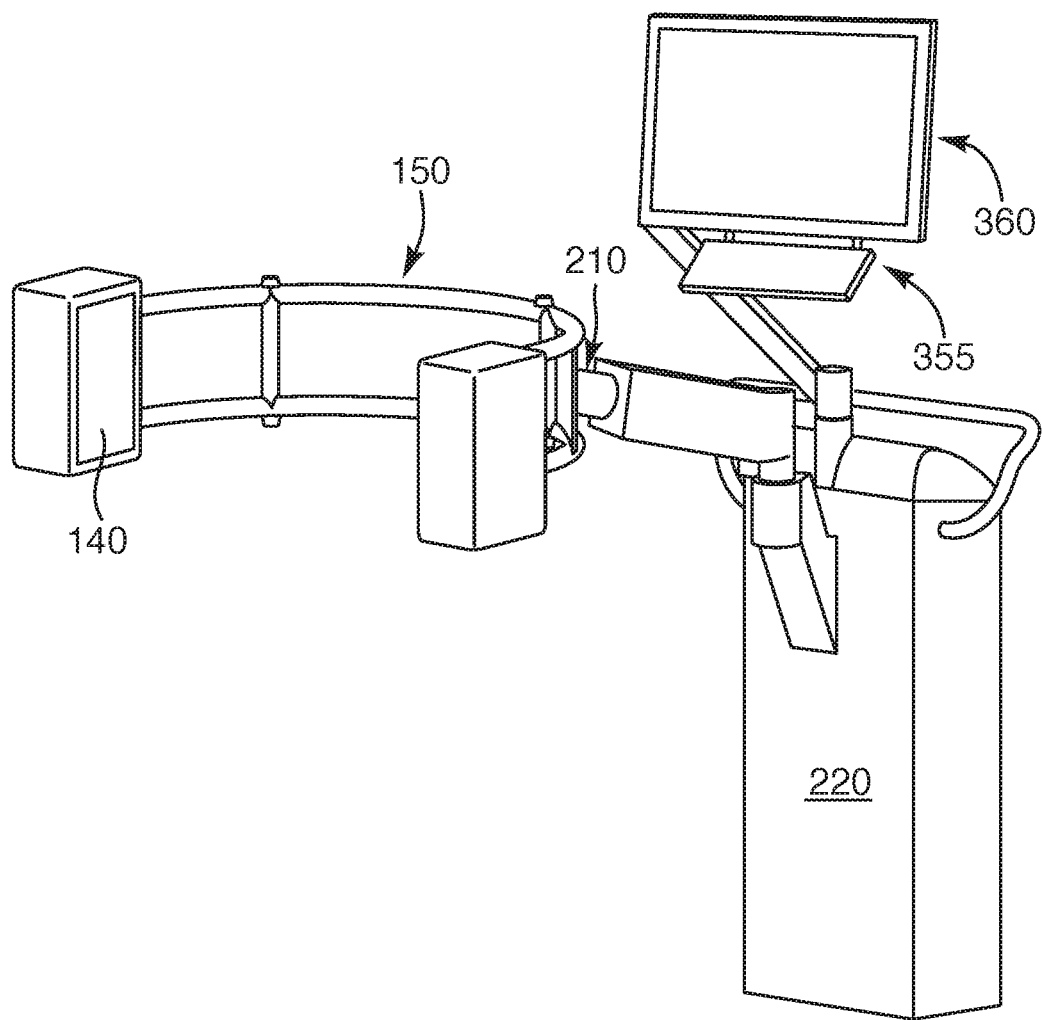
Figure 4:
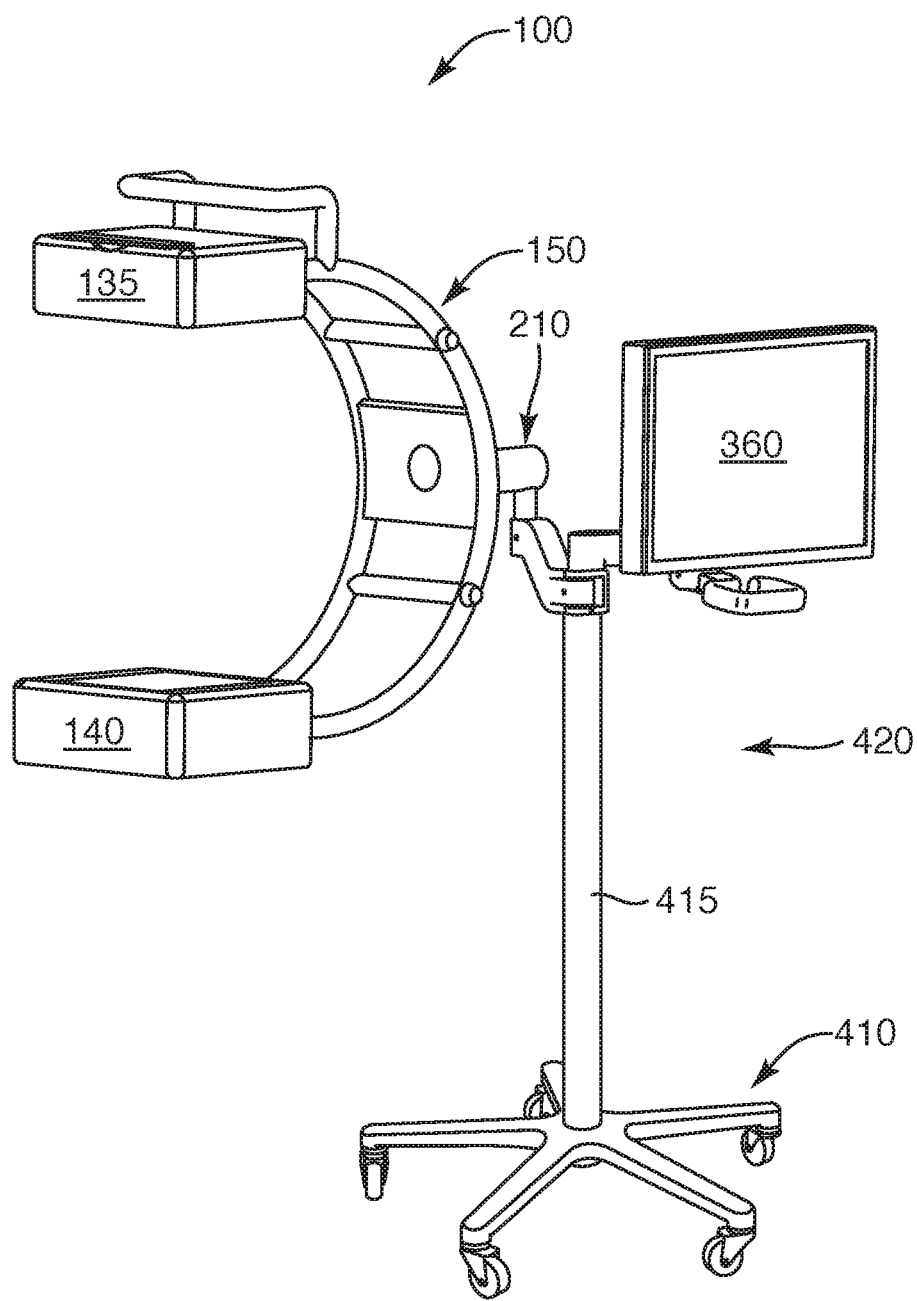
FIG. 4 shows other embodiments of supporting devices that can be used with small, portable X-ray devices.
Figure 5:
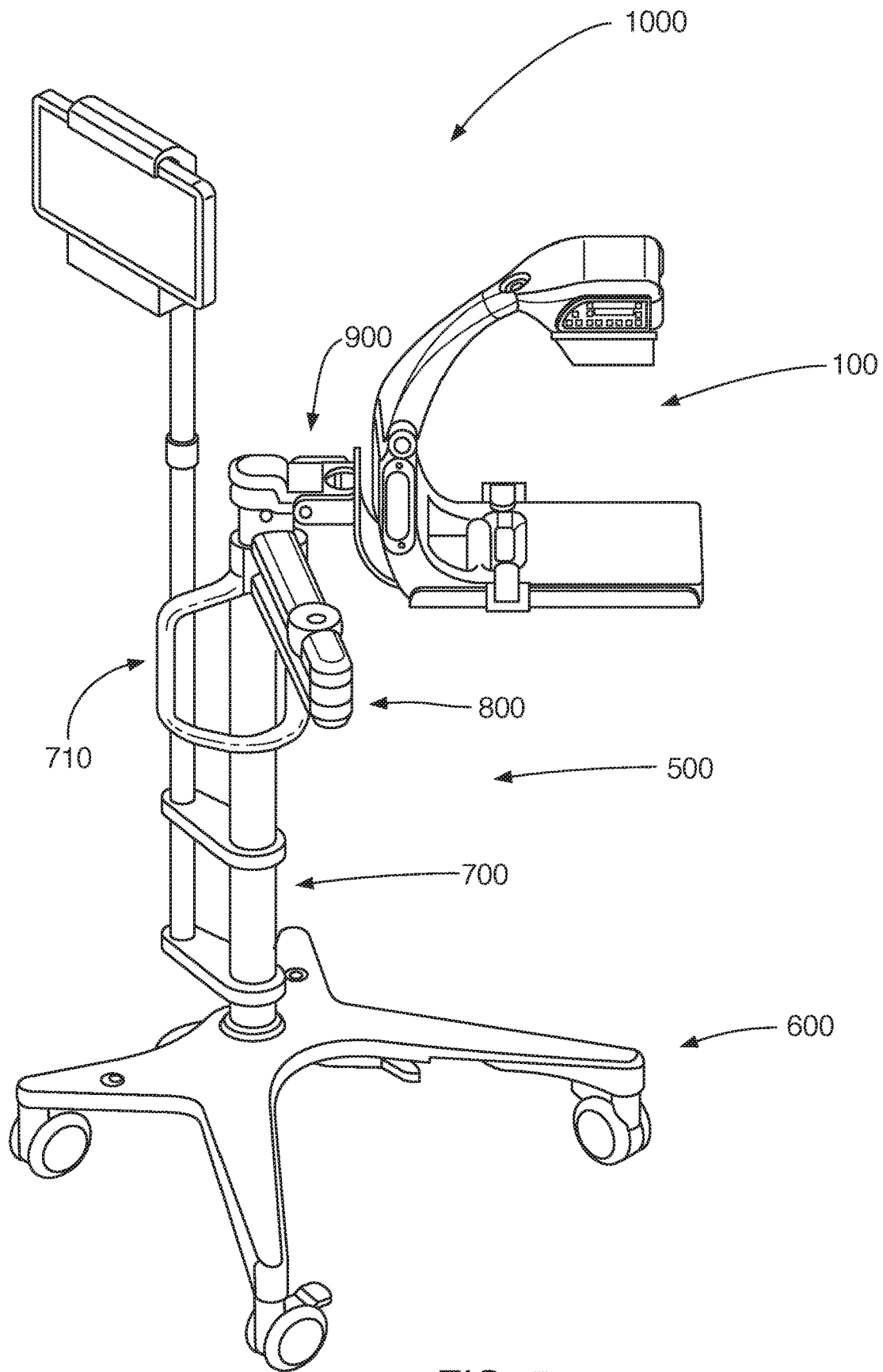
FIG. 5 illustrates yet other embodiments of a supporting device for holding small, portable X-ray devices.

In some embodiments, the portable x-ray device 100 can be connected to a stationary external (or support) structure so that it can rotate, or be positioned, around an object being analyzed, as shown in FIGS. 3A and 3B and as described in U.S. patent application Ser. No. 15/568,708, filed Nov. 23, 2017, the entire disclosure of which is incorporated herein by reference. In other embodiments, the portable x-ray device 100 can be connected to a mobile external (or support) structure for a similar purpose, as shown in FIGS. 4 and 5 as described in U.S. patent application Ser. No. 16/198,956, filed Nov. 23, 2018, the entire disclosure of which is incorporated herein by reference. Attaching the portable x-ray device to a support structure allows the operator to position the portable x-ray device 100 as needed for a series of imaging procedures, while freeing medical personnel to attend to other duties. As well, it leaves the hands of the operator free for other actions. For example, during a surgical procedure, attaching the portable x-ray device 100 to a support structure allows the medical person to take many actions, but then easily image the patient when needed using the pre-selected positioning of the portable x-ray device 100. When the surgical procedure is complete, the portable x-ray device 100 can be removed from the support structure and taken to another location for use or storage.

Figure 13:
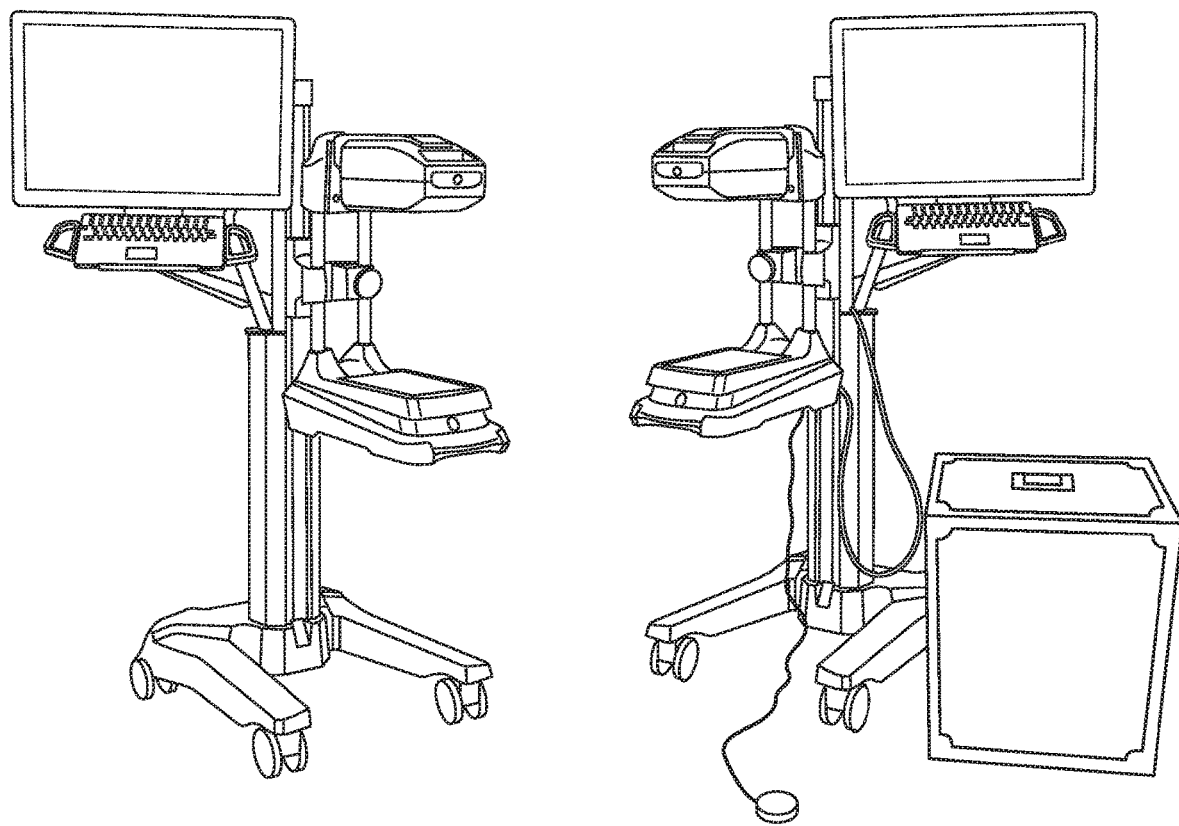
FIGS. 13-14 show some conventional supporting devices for x-ray devices.
Figure 14:
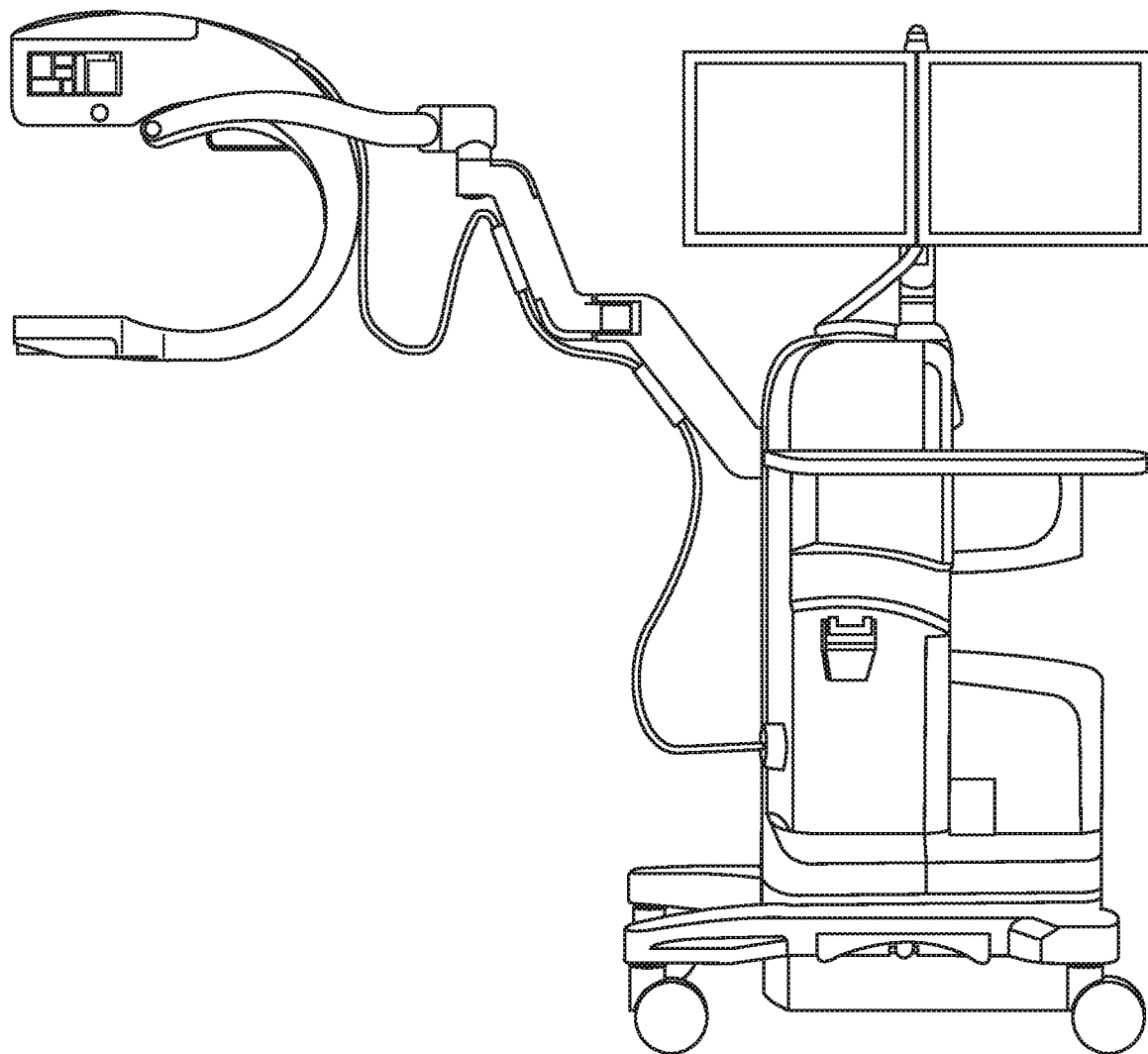

With some conventional support structures, though, removing the portable x-ray device 100 from the support structure is either not possible, or is not an easy or quick procedure. For example, with the conventional support structure shown in FIG. 13, the x-ray device can only be removed by loosening the clamp connecting it to rest of the system, but this action does not really release the x-ray device from the x-ray system since it is still connected to the support structure by power and data cables. Thus, it cannot be easily taken to a new location and it is not truly a portable x-ray device. And with the conventional support structure shown in FIG. 14, the c-arm x-ray device can't be even removed from the support structure.

To overcome these difficulties, the portable x-ray device 100 in some embodiments can be connected to an external (or support) structure using a connecting mechanism that is secure, yet also capable of being operated by one hand while the other hand holds the portable x-ray device 100 for safety during the connection process. Using such a connecting mechanism allows an operator to quickly and easily attach (and remove) the portable x-ray device 100 from the support structure and move it freely once disconnected, making the portable x-ray device 100 truly mobile.

Figure 6:
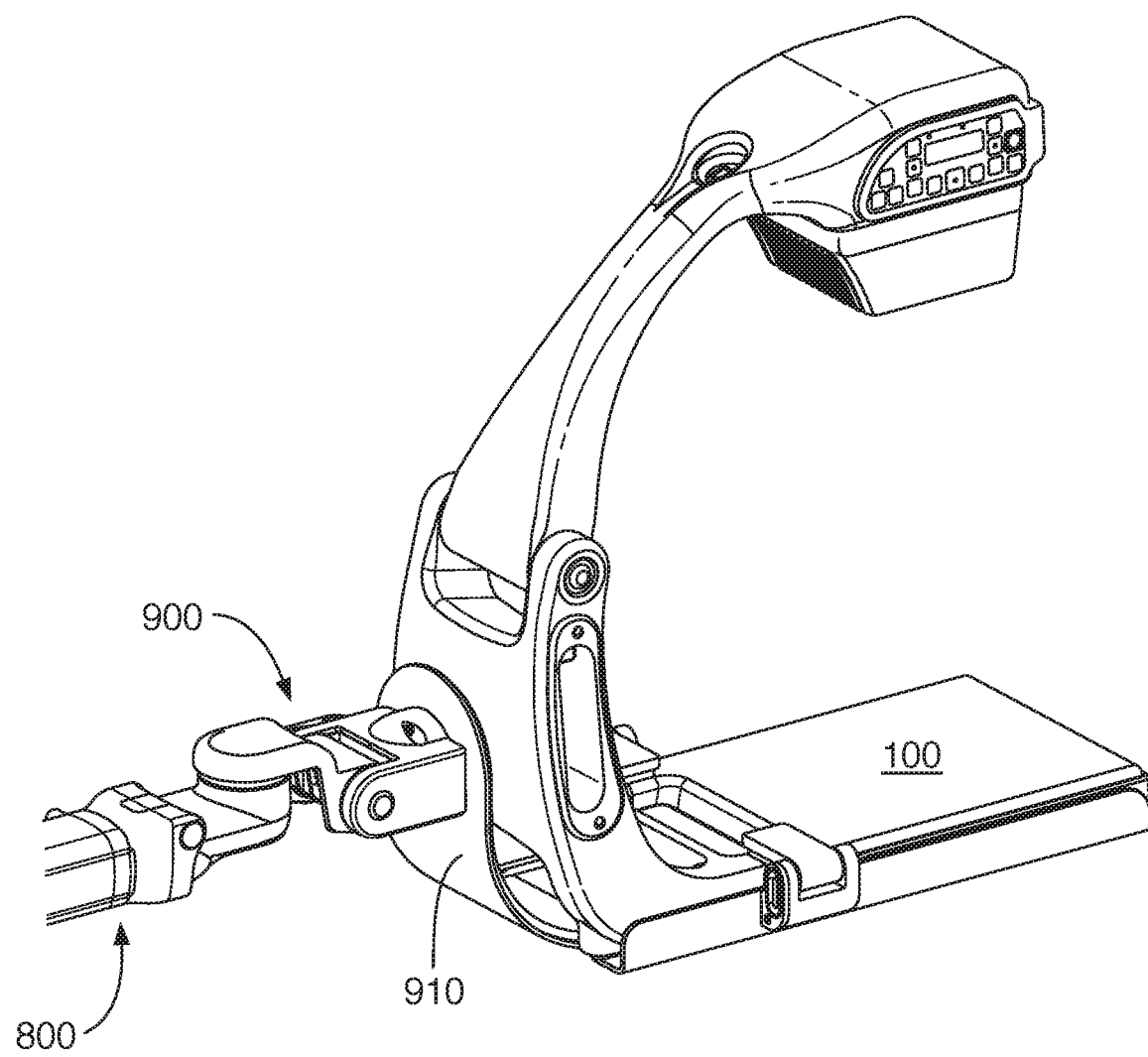
FIG. 6 illustrates some embodiments of a connecting member for attaching small, portable X-ray devices to a support structure.

In these embodiments, a connecting member 900 is used to flexibly connect the portable x-ray device 100 to any desired supporting structure. As shown in FIG. 6, an extension arm 800 of the support structure can be connected to an end of the connecting member 900. The other end of the connecting member is connected to a cradle 910 into which the portable x-ray device 100 rests. The cradle 910 is configured so that it has a surface that conforms to or meshes with the outer surface of the housing of the portable x-ray device 100 or any other desired part of the portable x-ray device 100. The portable x-ray device 100 can be attached and secured to the cradle 910 so that its position relative to the extension arm 800, and its orientation in three dimensions, is controlled by connecting member 900 during operation of the x-ray device 100. Once operation of the portable x-ray device 100 is concluded, the portable x-ray device 100 can be detached from the cradle 910.

Figure 7:
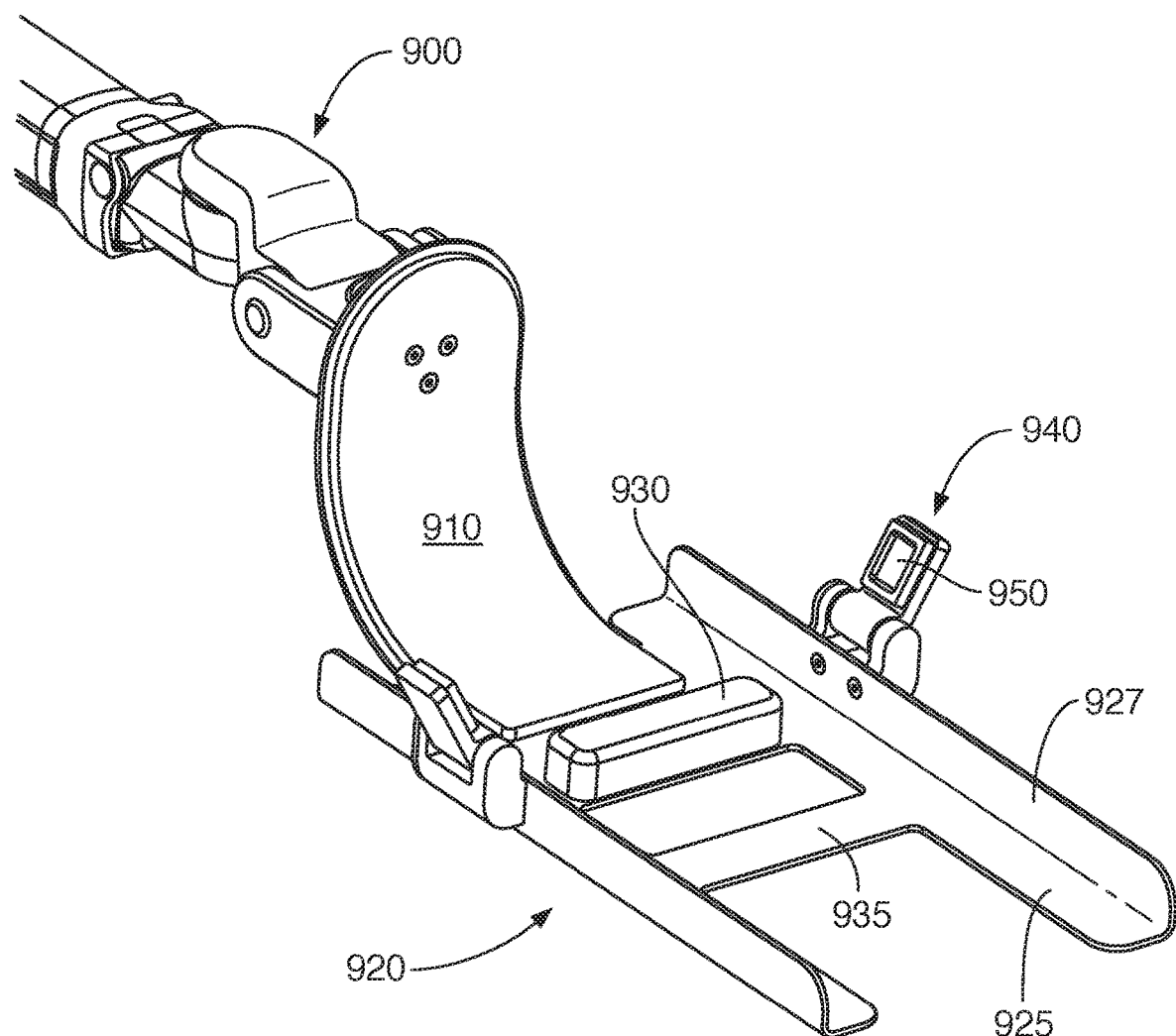
FIGS. 7-8 shows some embodiments of clamping mechanisms for attaching small, portable X-ray devices to a support structure.
Figure 8:
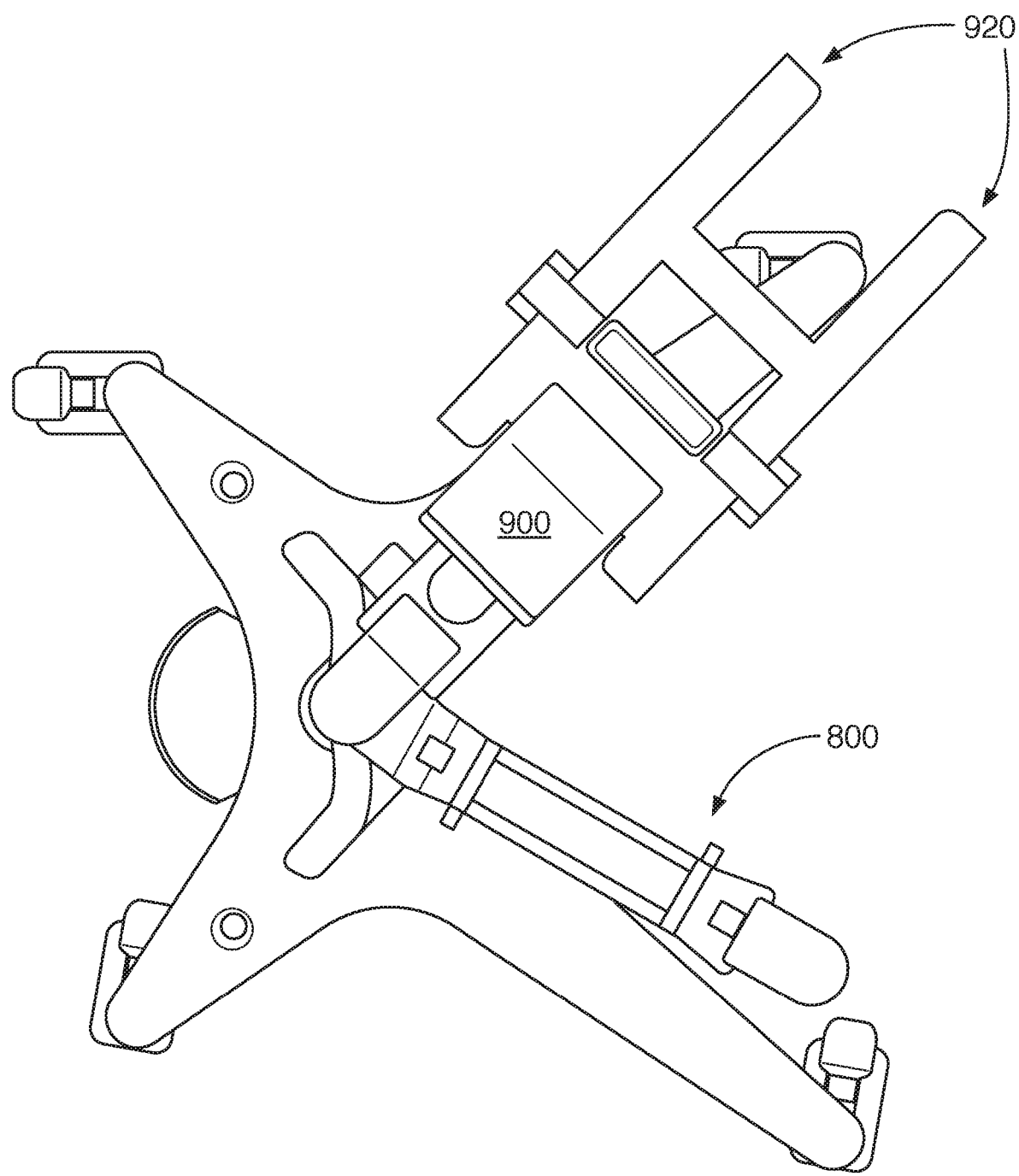

The cradle 910 also contains mounting plate(s) or support(s) 920 that are used to support the bottom of the portable x-ray device 100, as shown in the perspective view of FIG. 7 and the bottom view of FIG. 8. The mounting plates 920 are designed to support and contain the bottom of the portable x-ray device 100 when the portable x-ray device 100 rests on the cradle 910. So with the configuration of the portable x-ray device 100 shown in FIG. 2, the mounting plates 920 are configured to contain length members 925 with ridges 927 that are configured to extend along the length of the bottom sides of the portable x-ray device 100. The mounting plates 920 also contain width members 935 that extend between the length members 925. The width members are configured to extend along the width of the bottom of the portable x-ray device and provide rigidity to the mounting plates 920 and the entire cradle 910. While only two width members 935 are shown in FIGS. 7-8, the mounting plates 920 could have more or less than those shown in these Figures. Optionally, the mounting plates 920 could contain width members with ridges that could be located to extend along the width of the bottom sides of the portable x-ray device 100, thereby fully enclosing the bottom of the portable x-ray device.

The connecting member 900 also contains several features that can be used to secure or clamp the portable x-ray device 100 into place in the cradle 910 and the mounting plates 920. One of these features comprises insert 930 that is located near the middle of the mounting plates. The insert 930 extends upwards from the mounting plates 920 and is configured with a size and shape that mates with an opening 175 in the portable x-ray device 100. The mating of an opening 175 in the portable x-ray device 100 as depicted that accepts the insert 930 as depicted provides immediate registration and location of the portable x-ray device 100 accurately on the cradle 910. This is helpful for a quick attachment and/or quick release of the portable x-ray device 100. Without such a registration feature, the medical personnel operating the portable x-ray device 100 would spend precious time adjusting and positioning the portable x-ray device 100 on the cradle 910 instead of on the needed part of the medical procedure. And with such a registration feature, the registration is automatic.

In other embodiments, the registration insert 930 and matching opening 175 could be rectangular in shape, or circular, or oval, or any other shape that allows the combination of the opening 175 and the insert 930 together. As well, the height of the registration insert 130 (and the corresponding depth of the opening 175) can be modified from what is shown in the Figures. And while a single registration feature is shown in the Figures, multiple registration features with the same or different sizes and shapes (along with matching openings in the portable x-ray device 100) can be used. In other embodiments, the registration insert could be located on the portable x-ray device 100 and a matching insert could be located on the mounting plate(s).

Another securing feature in cradle 910 is the clamps 940. The clamps 940 are located on the ridges (or side stiffeners) 927 of the length members 925 of the mounting plates 920 so that they are situated on opposing sides of the bottom of the portable x-ray device 100. The clamps 940 can remain open when not used and closed on the portable x-ray device 100 when needed. Alternatively, the clamps 940 could be closed when not in use at the expense of an additional motion or moment of time to open them before x-ray device 100 could be mounted on the cradle 910. Examples of this opening and closing action are shown in FIGS. 9-12 where the clamps 940 are in an open position in FIG. 9, partially closed positions in FIGS. 10-11, and in a completely closed position in FIG. 12 to secure the portable x-ray device 100 to the cradle 910 and mounting plates 920.

The clamps 940 can be configured to meet multiple requirements. One requirement is to have at least two independent failure points in securing the portable x-ray device 100 to the cradle 910. This functionality can be accomplished in part by requiring that each of the clamps 940 have a separate release button, lever, or other mechanism that releases the clamp 940 from the portable x-ray device 100. Thus, if one of the clamps 940 is accidently opened or were to fail, the other clamp, combined with the physical registration or constraining action of the insert 930 in the opening 175, would ensure that the portable x-ray device 100 cannot slip or fall from the cradle 910, even if it is no longer snuggly or firmly fixed in the cradle 910.

This functionality demonstrates another benefit obtained by using the insert 930. Not only does insert 930 register the portable x-ray device 100 as described herein, but it also acts to help secure the x-ray device 100 in the cradle 910 against accidental release. In order to accomplish this function, the insert 930 should mesh snuggly and reasonably tight within the opening 175. But if the fit is too tight, then the portable X-ray device 100 will be difficult to mount or remove from the cradle 910. Yet if the fit is too loose, the insert 930 may not act appropriately as part of the secure mounting system described herein. So a balanced fit has to be used.

In other embodiments, additional clamps 940 could be used on the mounting plates 920 so that that the cradle 910 contains 3, 4 or even more clamps. Additional clamps could be positioned on the bottom of cradle 910 to clamp the portable x-ray device 100 by securing the length members 925 of the C-arm against the mounting plates 920, or by mounting them in other ways. However, the use of more than 2 clamps may not be needed in some embodiments since additional clamps will complicate the mounting or removal of the portable x-ray device 100 to the cradle 910 without providing additional security or physical stability beyond that provide by just using two clamps.

In other configurations, the clamps 940 and the portable x-ray device 100 can be provided with matching features to help the clamping function. For example, the clamps 940 depicted in FIG. 7 contain extensions 950 that are flexible and compress when the clamps 940 are secured on the housing of the portable x-ray device 100 in order to provide some positive pressure on the x-ray device 100 to keep it firmly seated. But the extensions 950 could also be configured to be inflexible and mated to matching indentations in the portable x-ray device (not shown).

The clamps 940 can be actuated or applied to the portable x-ray device 100 in any number of ways. It is possible for the clamps 940 to be spring loaded such that they snap shut on the x-ray device 100 when actuated by a button, a lever, or some other feature. Alternatively, the clamps 940 could be actuated by a clamping lever (not shown) that would work within the clamping mechanism to close the clamps and apply pressure to secure the x-ray device 100. In other embodiments, the clamps 940 could be designed to contain an internal ratchet mechanism (or similar functionality) that is light enough in action that the clamps can be pressed or squeezed closed using one hand and the pressure of the fingers and palms and retain the clamps 940 in the closed position automatically, retaining the pressure against the portable x-ray device 100 that was initially imparted by hand. This ratchet mechanism can also be configured to only partially open when initially released by the operator using the button, lever, or other actuator, so that the C-arm of the portable x-ray device 100 can't fall out of the cradle 910 until the clamp 940 has been fully released with a second activation of the release mechanism.

Figure 9:
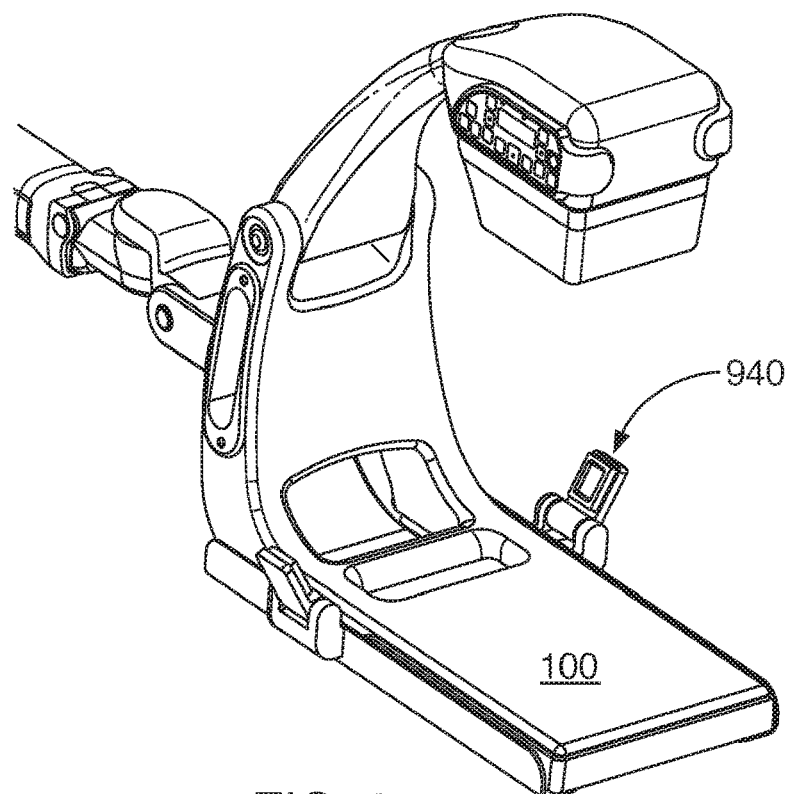
FIGS. 9-12 shows some embodiments of opened and closed clamping mechanisms for attaching small, portable X-ray devices to a support structure.
Figure 10:
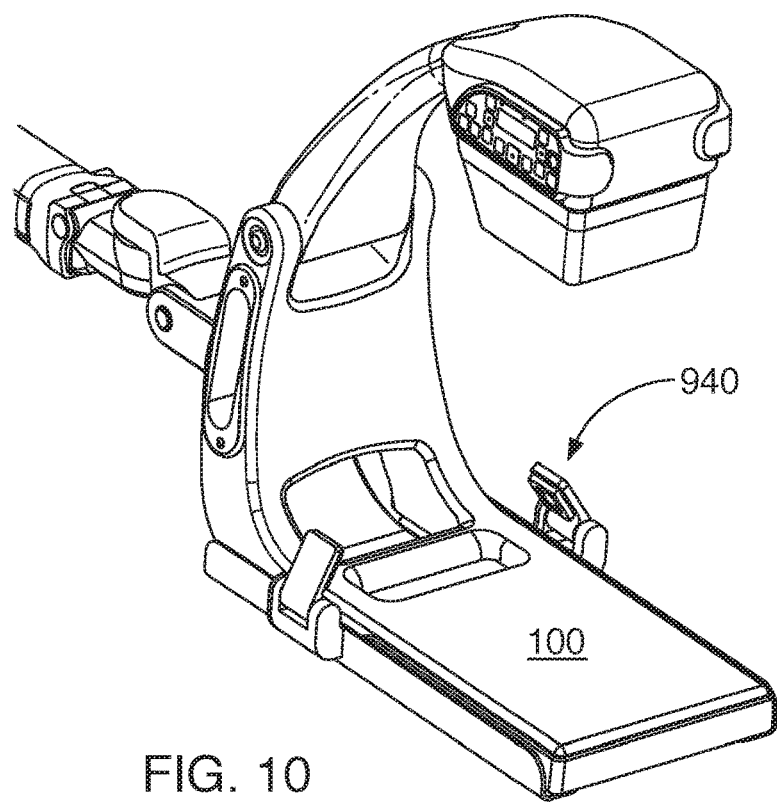
Figure 11:
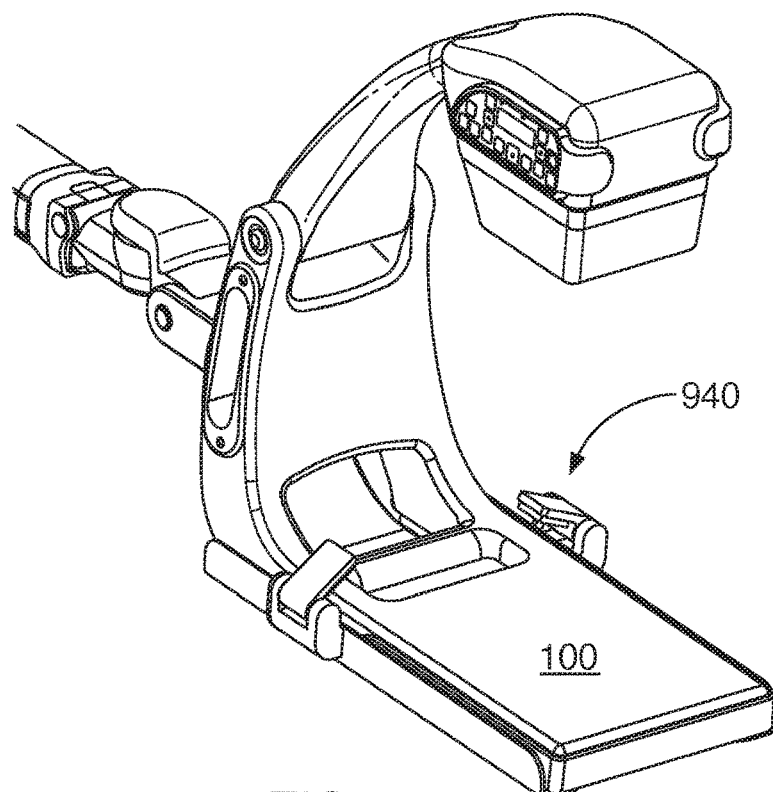
Figure 12:
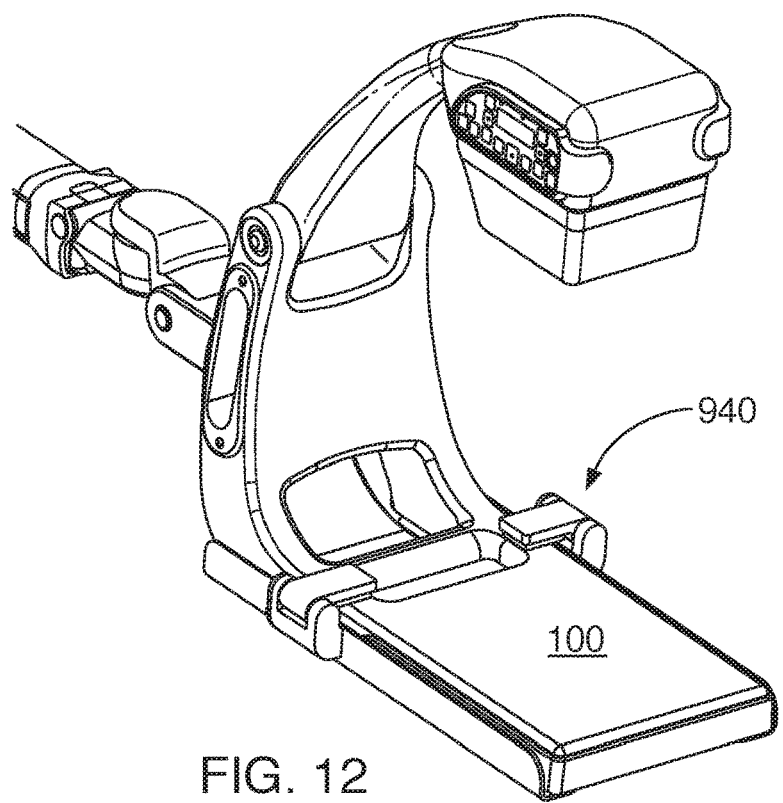

The portable x-ray device 100 can quickly and easily be attached and removed from the cradle 910 and mounting plates 920 using a single hand by an average sized operator in the following manner. When the clamps 940 are in the open position shown in FIG. 7, the portable x-ray device can be carried by hand and placed onto the cradle and mounting plates so that the insert 930 fits within the opening 175, as shown in FIG. 9. The clamps 940 can then be closed by an operator, as shown in FIGS. 10-12. The portable x-ray device 100 can then be operated to take an x-ray image of the patient without the medical personnel constantly holding the portable x-ray device 100. When needed, the clamps 940 can be opened by pressing the button or otherwise activating the release mechanism, and then the portable x-ray device 100 can be easily lifted off the cradle/mounting plates using only a single hand by the average person.

When the portable x-ray device 100 is attached to the cradle and mounting plates, it can be used in imaging procedures of a patient. Some of those imaging procedures can be performed during a surgical procedure where a sterile field needs to be maintained. One manner of maintaining a sterile field is by using a sterile bag around the portable x-ray device 100. To keep the sterile field, the clamps 940 and the insert 930 must be configured so that such a sterile bag is not punctured when the clamps are closed.

In some configurations, the connecting member 900 containing the cradle 910 is connected to a supporting device, such as a support stand. The support stand that is attached to and supports the cradle 910 through connection member 900 will intentionally or may accidentally be brought close to the patient. To maintain a sterile field near the patient, a sterile bag can be placed over the support stand and the cradle 910 before the portable x-ray device 100, in a separate sterile bag, is mounted or placed in the cradle 910. In other words, two sterile bags can be used: a first sterile bag covering the cradle 910, the connecting member 900, and the rest of the support stand as appropriate, and a second sterile bag around the portable x-ray device 100 itself. Such a configuration will allow the portable x-ray device 100 to be maintained sterile, while simultaneously allowing for the rapid and easy removal of the portable x-ray device 100 during the medical procedure.

This requirement of using two sterile bags in these embodiments can introduce additional constraints on the insert 930, the clamps 940, and even on the mounting plates 920, as well as other components of the portable x-ray device 100, especially the opening 175. The first constraint is that all of these features, whether part of the cradle 910, the x-ray device 100, or the clamps 940, must be designed with rounded surfaces, chamfers, or other means to smooth corners and edges so that the sterile bags cannot be caught and torn, or punctured. In some configurations, the corners, edges, chamfers, and other rounding of features have a minimum radius no smaller than about 0.5 mm, with about 1.0 mm or about 2.0 mm as a more practical minimum since the sharper the corner (i.e., the smaller the radius), the more easily a polymer film sterile bag can be torn or inadvertently penetrated. The minimum corner radius also depends on the shape of the feature. If, for example, the feature is a flat plate or surface that is only 2 mm or 3 mm thick, the corner radius will essentially become a flat circle with a radius of one half the thickness of the plate. This configuration would be the case for many handles, levers, and other such features.

It is also desirable that all surfaces must have some significant area so that there is no feature (including features such as handles, clamping levers, and similar devices) that is capable of, or likely to, puncture the sterile bag if the bag is stretched across the physical feature. So handles, clamping levers, and similar devices can be designed or angled to lie close to the adjacent surface in order to avoid any features that poke out from the over-all device at large angles of about 60 degrees, about 70 degrees, about 80 degrees, or about 90 degrees. Handles, clamping levers, and similar devices should also have a rounded end with a radius of at least about 2 mm, about 3 mm, about 4 mm, or even about 5 mm in order to avoid punctures of the sterile bag polymer sheet. Additionally, any hinges, such as in the clamps 940 must be designed to ensure that a thin plastic sheet or membrane from a sterile bag cannot be caught, torn, or punctured by the operation of the clamps 940.

An additional constraint is that the clamp 940 must be able to accommodate the variations in the clamping conditions caused by the absence of any sterile bags, or the presence of 1, 2, 3 4, 5, or even more layers of plastic between the x-ray device 100 and the cradle 910, clamps 940, and/or resilient pads 950. These intervening layers can be caused by sterile drapes on the support stand and/or the portable x-ray device 100 since one or more folds in the sterile bag material might be captured between the x-ray device 100 and the cradle 910, clamps 940, and/or resilient pads 950. These folds can be introduced because sterile drapes are designed to be somewhat loose and baggy to allow for the quick application of the sterile bag over the component to be rendered (or maintained) sterile. This looseness is often dealt with by gathering some folds together at various locations of the component that is covered by the sterile bag.

Therefore, the clamps 940 and the resilient pads 950 need to be able to accommodate a variety of clamping conditions. For example, if the sterile bag material is 5 thousandths of an inch (i.e., 5 mils or 0.127 mm) thick, the clamping mechanism needs to be able to successfully and adequately clamp the portable x-ray device 100 with the variation in the total effective material thickness ranging from 5 mils, to 10 mils, 15 mils, 20 mils, 25 mils, 30 mils, or even more. Converting to millimeters, the equivalent thickness could vary by about 0.1 mm, to 0.2 mm, 0.3 mm, 0.4 mm, 0.5 mm, up to 0.6 mm, 0.7 mm, or even more. The resilience that the clamping mechanism needs to deal with such a broad variation in thickness could be designed into the pad 950 by using rubber, foam, foam rubber, or similar material. It also could be designed into a combination of the pad 950, the clamp 940 and its mechanism, and/or even into the design of the cradle 910 by incorporating a resilient foam, or rubber, or other such resilient material into the cradle 910 by placing it on the length members 925 and width members 935.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner

The invention claimed is:

1. A clamping device for a portable X-ray device having a C-arm and a bottom, comprising:
    a cradle configured to abut and support a C-arm of the portable x-ray device;
    a mounting plate configured to support a bottom portion of the portable x-ray device, the mounting plate having length members with ridges and a width member extending between the length members;
    a registration insert configured to mate with an opening in the portable x-ray device; and
    two clamps configured to secure the portable x-ray device to the cradle and the mounting plate.

2. The device of claim 1, wherein the cradle is connected to a supporting structure for the portable x-ray device.

3. The device of claim 1, wherein the portable x-ray device is capable of being removed from the clamping device using a single hand.

4. The device of claim 3, wherein the clamps comprises a release that can be manually activated by a single hand.

5. The device of claim 4, wherein the release contains a ratchet mechanism that only partially releases the clamps and fully releases the clamps using a second activation.

6. The device of claim 1, wherein the mounting plate constrains a bottom of the portable x-ray device when it abuts the cradle.

7. The device of claim 1, wherein the clamps are located on opposing sides of the bottom of the portable x-ray device.

8. The device of claim 1, wherein the clamps contain extensions that are flexible and compress when secured on the portable x-ray device.

9. The device of claim 1, wherein the cradle, mounting plate, registration insert, and/or clamps are configured with rounded surfaces and smooth corners.

10. An x-ray system, comprising:
    a portable X-ray device having a C-arm and a bottom;
    a supporting structure for the portable X-ray device;
    a clamping device comprising:
        a cradle configured to abut and support a C-arm of the portable x-ray device;
        a mounting plate configured to support a bottom portion of the portable x-ray device, the mounting plate having length members with ridges and a width member extending between the length members;
        a registration insert configured to mate with an opening in the portable x-ray device; and
        two clamps configured to secure the portable x-ray device to the cradle and the mounting plate.

11. The system of claim 10, wherein the supporting structure comprising an extension arm.

12. The system of claim 11, wherein the cradle is connected to the extension arm of the supporting structure.

13. The system of claim 10, wherein the portable x-ray device is capable of being removed from the clamping device using a single hand.

14. The system of claim 10, wherein the mounting plate constrains a bottom of the portable x-ray device when it abuts the cradle.

15. The system of claim 10, wherein the clamps are located on opposing sides of the bottom of the portable x-ray device.

16. The system of claim 15, wherein the clamps comprises a release that can be manually activated by a single hand.

17. The system of claim 16, wherein the release contains a ratchet mechanism that only partially releases the clamps and full releases the clamps using a second activation.

18. The system of claim 10, wherein the clamps contain extensions that are flexible and compress when secured on the portable x-ray device.

19. The system of claim 10, wherein the cradle, mounting plate, registration insert, and/or clamps are configured with rounded surfaces and smooth corners.

20. A method of imaging, comprising:
    attaching a portable x-ray device having a C-arm and a bottom to a supporting structure with a single hand using a clamping device comprising:
        a cradle configured to abut and support a C-arm of the portable x-ray device;
        a mounting plate configured to support a bottom portion of the portable x-ray device, the mounting plate having length members with ridges and a width member extending between the length members;
        a registration insert configured to mate with an opening in the portable x-ray device; and
        two clamps configured to secure the portable x-ray device to the cradle and the mounting plate;
    closing the clamps on the portable x-ray device; and
    imaging an object using the portable x-ray device.

21. The method of claim 20, further comprising removing the portable x-ray device from the supporting device using a single hand by opening the clamps.

* * * * *